(12) United States Patent
Cannata et al.

(10) Patent No.: US 7,199,266 B2
(45) Date of Patent: Apr. 3, 2007

(54) PROCESS FOR THE PREPARATION OF GABAPENTIN

(75) Inventors: Vincenzo Cannata, Sasso Marconi (IT); Andrea Nicoli, Vicenza (IT); Francesco Corcella, Rozzano (IT)

(73) Assignee: Zambon Group S.p.A., Vicenza (IT)

( * ) Notice: Subject to any disclaimer, the term of this patent is extended or adjusted under 35 U.S.C. 154(b) by 341 days.

(21) Appl. No.: 10/399,409

(22) PCT Filed: Oct. 15, 2001

(86) PCT No.: PCT/EP01/11867

§ 371 (c)(1),
(2), (4) Date: Nov. 25, 2003

(87) PCT Pub. No.: WO02/34709

PCT Pub. Date: May 2, 2002

(65) Prior Publication Data

US 2004/0068011 A1 Apr. 8, 2004

(30) Foreign Application Priority Data

Oct. 23, 2000 (IT) .................................... MI2000A2285

(51) Int. Cl.
*C07C 229/00* (2006.01)

(52) U.S. Cl. ..................................................... 562/507
(58) Field of Classification Search ................ 560/125; 562/502

See application file for complete search history.

(56) References Cited

U.S. PATENT DOCUMENTS

| 4,024,175 A | | 5/1977 | Satzinger et al. |
| 4,087,544 A | * | 5/1978 | Satzinger et al. ........... 514/530 |
| 4,691,054 A | | 9/1987 | Tosa et al. |
| 5,279,744 A | | 1/1994 | Itoh et al. |

FOREIGN PATENT DOCUMENTS

| EP | 0 414 263 | 2/1991 |
| ES | 2 063 219 | 2/1991 |
| GB | 1145512 | 3/1969 |
| JP | 8-183768 | 7/1996 |
| WO | WO 00/64857 | 2/2000 |
| WO | WO 02/34709 | 5/2002 |
| WO | WO 03/089403 | 10/2003 |

OTHER PUBLICATIONS

CAS Abstr. No. 1988:95088, IN 158937, Feb. 21, 1987.
Patent Abstracts of Japan, JP 58–210027, Dec. 7, 1983.
S.R. Dye et al.: "Equilibrium sorption of amino acids by a cation–exchange resin" Industrial & Engineering Chemistry Research, vol. 29, No. 5, pp. 849–857 May 1, 1990.
CAS Abstr. No. 1988:95088, IN 158937, Feb. 21, 1987.
Patent Abstracts of Japan, JP 58–210027, Dec. 7, 1983.

* cited by examiner

*Primary Examiner*—Paul A. Zucker
(74) *Attorney, Agent, or Firm*—Oblon, Spivak, McClelland, Maier & Neustadt, P.C.

(57) ABSTRACT

A process for the purification of gabapentin by treatment of a crude aqueous gabapentin hydrochloride solution with a strong cationic ion exchange resin.

11 Claims, No Drawings

PROCESS FOR THE PREPARATION OF GABAPENTIN

BACKGROUND OF THE INVENTION

1. Field of the Invention

The present invention relates to a process for the preparation of gabapentin and, more particularly, it relates to a process for the purification of gabapentin hydrochloride and for its conversion into gabapentin by treatment with a strong cationic ion exchange resin.

2. Description of the Background

Gabapentin, 1-(aminomethyl)cyclohexaneacetic acid (The Merck Index, XII Ed., page 733, No. 4343), is a known drug with anti-epileptic activity described for the first time by Warner-Lambert Co. in the U.S. Pat. No. 4,024,175.

In the literature several processes for the preparation of gabapentin are reported (see for example the U.S. Pat. Nos. 4,024,175, 5,068,413 and 5,091,567).

Substantially all these methods foresee a final step of gabapentin purification that consists in the treatment of an aqueous solution of a gabapentin salt (generally hydrochloride) through a weak basic ionic exchange resin, the complete evaporation of water from the aqueous gabapentin solution eluted from the resin and the crystallization from an alcoholic solvent, generally methanol or methanol/isopropanol or ethanol/ether mixtures.

Several alternative methods to the use of the weak basic ionic exchange resin for the conversion of gabapentin hydrochloride into gabapentin have been described.

In patent application WO 98/28255 (Teva) a process for the preparation of gabapentin from the corresponding hydrochloride is described which comprises the purification of gabapentin hydrochloride from the inorganic salts deriving from the synthesis by (a) solubilization of gabapentin hydrochloride in organic solvents wherein the inorganic salts are insoluble, (b) filtration and (c) optional evaporation of the solvent; the treatment of a gabapentin hydrochloride solution with an amine in a solvent so as to precipitate gabapentin form III and the crystallization to obtain gabapentin form II.

In patent application WO 00/58268 (Bioindustria Laboratorio Italiano Medicinali S.p.A.) the separation of the inorganic salts from gabapentin is carried out by diafiltration.

SUMMARY OF THE INVENTION

We have now found an alternative process for purifying gabapentin hydrochloride from the inorganic salts and obtain gabapentin, which uses strong cationic ion exchange resins.

Therefore, object of the present invention is a process for the purification of gabapentin hydrochloride from the inorganic salts and for its conversion in gabapentin by treatment of an aqueous gabapentin hydrochloride solution through an ion exchange resin characterized by the fact that the ion exchange resin is a strong cationic resin.

The process object of the present invention allows to obtain gabapentin form II directly from an aqueous gabapentin hydrochloride solution containing inorganic salts by carrying out the purification and conversion in a single step through the use of the strong cationic resin.

Generally the aqueous gabapentin hydrochloride solution used in the process object of the present invention comes directly from the reaction mixture used to synthetize gabapentin after usual work-up (extraction and/or crystallization).

The inorganic salts present in the aqueous gabapentin hydrochloride solution are generally sodium salts, in particular sodium chloride.

Gabapentin hydrochloride can be prepared with one of the synthetic methods described in the literature, but it is preferably prepared using one of the synthetic processes described in U.S. Pat. No. 4,024,175.

Examples of strong cationic resins are IRA 120, DIAION SK 18, IMAC HP 1110.

The process object of the present invention comprises a first step of fixing gabapentin to the resin using water as eluant. In this first step both gabapentin and sodium are fixed to the resin, removing then the chlorides and the possibly present residual organic solvents.

In the second step, the resin is eluted with an ammonia solution allowing the selective release of gabapentin from the resin, in a form substantially devoid of inorganic salts which can be isolated by evaporation and subsequent crystallization. The ammonia solution used in the release step is preferably a solution with a concentration equal to or less than 4%.

A preferred embodiment of the process object of the present invention is the following.

An aqueous solution containing gabapentin, gabapentin hydrochloride and sodium chloride is fixed to a column containing a strong cationic resin of sulphonic type eluting then with water to remove the chlorides. The elution of the resin is then continued with an ammonia solution and then with water collecting the fractions containing gabapentin. The fractions are then concentrated by distillation up to obtaining a thick residue from which gabapentin is isolated by crystallization from alcoholic solvents according to known methods.

In order to better illustrate the present invention the following examples are now given.

DETAILED DESCRIPTION OF THE PREFERRED EMBODIMENTS

EXAMPLE 1

Demineralized water (146 Kg) and sodium hydroxide in about 30% solution (about 140 Kg) were charged in a reactor. Then 1,1-cyclohexanediacetic acid monoamide (190 Kg) was charged portionwise under stirring keeping the temperature between 0° C. and 25° C. After keeping under stirring for about 2 hours at 20–25° C. a solution was obtained.

In a second reactor sodium hydroxide in about 30% solution (about 140 Kg) and, while keeping the temperature below 20–25° C., 13% sodium hypochlorite (557 Kg) were charged, under vacuum and stirring. The previously prepared solution of 1,1-cyclohexanediacetic acid monoamide was added in about 2.5/4 hours keeping under a light nitrogen flux and cooling at an internal temperature of about −5° C. The mixture was maintained for about 2 hours at −3/+5° C. and raised then slowly to 20° C. in about 2–3 hours; keeping then at 20–25° C. for about 1 hour.

At the end of the reaction and after having destroyed the possible excess of oxidant with sodium metabisulphite, a solution of hydrochloric acid (about 250 Kg) was added up to pH 5±0.2, controlling the foam and the development of carbon dioxide, keeping the temperature at the room value.

During the addition of hydrochloric acid, at pH about 8–9, n-butanol (150 Kg) was charged and then the addition was continued.

At the end of the acid addition (pH 5±0.2), the mixture was kept under stirring for about 30 minutes regulating the temperature at about 20° C. and left then at rest for about 1 hour. The aqueous phase was separated at the temperature of about 20° C. and treated with n-butanol (150 Kg) and with a hydrochloric acid solution (about 35 Kg) up to pH 3.5±0.2. After keeping under stirring for about 30 minutes and controlling again the pH (2±0.2), the mixture was left to rest for about 1 hour and the aqueous phase was separated at the temperature of about 20° C. and treated with n-butanol (150 kg) and with a hydrochloric acid solution (about 15 kg) up to pH 2±0.2. After keeping under stirring for 30' and controlling the pH (2±0.2), the mixture was left to rest for about 1 hour and then the aqueous phase was separated at the temperature of about 20° C.

Water (1000 Kg) was added to the gathered butanolic phases (containing gabapentin, gabapentin hydrochloride and NaCl) and the obtained biphasic solution was eluted through a column containing a strong cationic resin (IMAC HP 1110). At the end of the biphasic solution elution, the column was further eluted with water (about 1500/1800 Kg) up to obtain at the exit Bx≦0.3.

The column was then eluted with an ammonia solution prepared from 28% ammonia (156 Kg) and water (1290 Kg). At the end of the elution with the ammonia solution, the process was continued with water (about 1200/1300 Kg) up to obtain Bx~0.3.

In this way about 1600 liters of gabapentin ammonia solution were collected, after discarding the dead volume (fractions which do not contain gabapentin).

The ammonia solution was filtered and concentrated by distillation under vacuum with internal temperature below 40° C. up to a thick solid residue.

Methanol (95 Kg) was added to the residue in four portions and the mixture was heated with water thermoregulated in jacket at 55–60° C. for about 1 hour. Isopropylic alcohol (395 Kg) was added to the obtained homogeneous suspension in about 20/30 minutes, with circulation of water thermoregulated at 60–65° C. At the end of the addition, the mixture was kept under stirring for about 30/60 minutes, always with circulating water thermoregulated at about internal temperature 55° C., and then it was cooled first with water and then with saline solution at internal temperature about −5° C. After keeping at this temperature for at least 1 hour, centrifugating and washing with isopropyl alcohol, about 130–140 Kg of wet product were obtained which were dried under vacuum at 50–55° C. for about 24 hours obtaining about 120–130 Kg of gabapentin.

EXAMPLE 2

Results analogous to example 1 were obtained by isolating gabapentin hydrochloride by crystallization, by treating the reaction mixture, after having destroyed the possible excess of oxidant, with concentrated hydrochloric acid (about 300 Kg) up to pH 1±0.5 and by seeding with gabapentin hydrochloride. The so obtained solid was dissolved in water (about 100 Kg) and the solution was treated with a strong cationic resin as described in example 1.

What is claimed is:

1. A process for producing gabapentin, comprising:
   (1) reacting 1,1-cyclohexanediacetic acid monoamide with an aqueous solution of sodium hydroxide and sodium hypochlorite, to obtain a first reaction mixture;
   (2) adding sodium metabisulfite to said first reaction mixture, to obtain a second reaction mixture; and
   (3) adding hydrochloric acid to said second reaction mixture, to obtain a third mixture comprising gabapentin hydrochloride and at least one inorganic salt.

2. The process of claim 1, wherein said (1) reacting 1,1-cyclohexanediacetic acid monoamide with sodium hydroxide and sodium hypochlorite, to obtain a first reaction mixture is carried out by mixing an aqueous solution of 1,1-cyclohexanediacetic acid monoamide with sodium hydroxide with an aqueous solution of sodium hydroxide and sodium hypochlorite.

3. The process of claim 2, wherein said aqueous solution of 1,1-cyclohexanediacetic acid monoamide and sodium hydroxide is formed by adding 1,1-cyclohexanediacetic acid monoamide to an aqueous solution of sodium hydroxide at a temperature of 0° C. to 25° C.

4. The process of claim 2, wherein said mixing is carried out with cooling.

5. The process of claim 4, wherein said mixing is carried out while cooling the first reaction mixture to an internal temperature of about −5° C.

6. The process of claim 4, wherein said first reaction mixture is raised to a temperature of 20° C. to 25° C.

7. The process of claim 2, wherein said mixing is carried out over a time of 2.5 to 4 hours.

8. The process of claim 2, wherein said mixing is carried out under nitrogen.

9. The process of claim 1, wherein said aqueous solution of sodium hydroxide and sodium hypochlorite is formed by adding sodium hypochlorite to an aqueous solution of sodium hydroxide at a temperature below 25° C.

10. The process of claim 1, wherein said inorganic salt is NaCl.

11. The process of claim 1, further comprising:
   (4) treating a mixture comprising gabapentin hydrochloride and at least one inorganic salt with a cationic exchange resin.

* * * * *